Nov. 15, 1960 H. C. SWIM ET AL Plant Pat. 1,985
ROSE PLANT
Filed Feb. 4, 1960
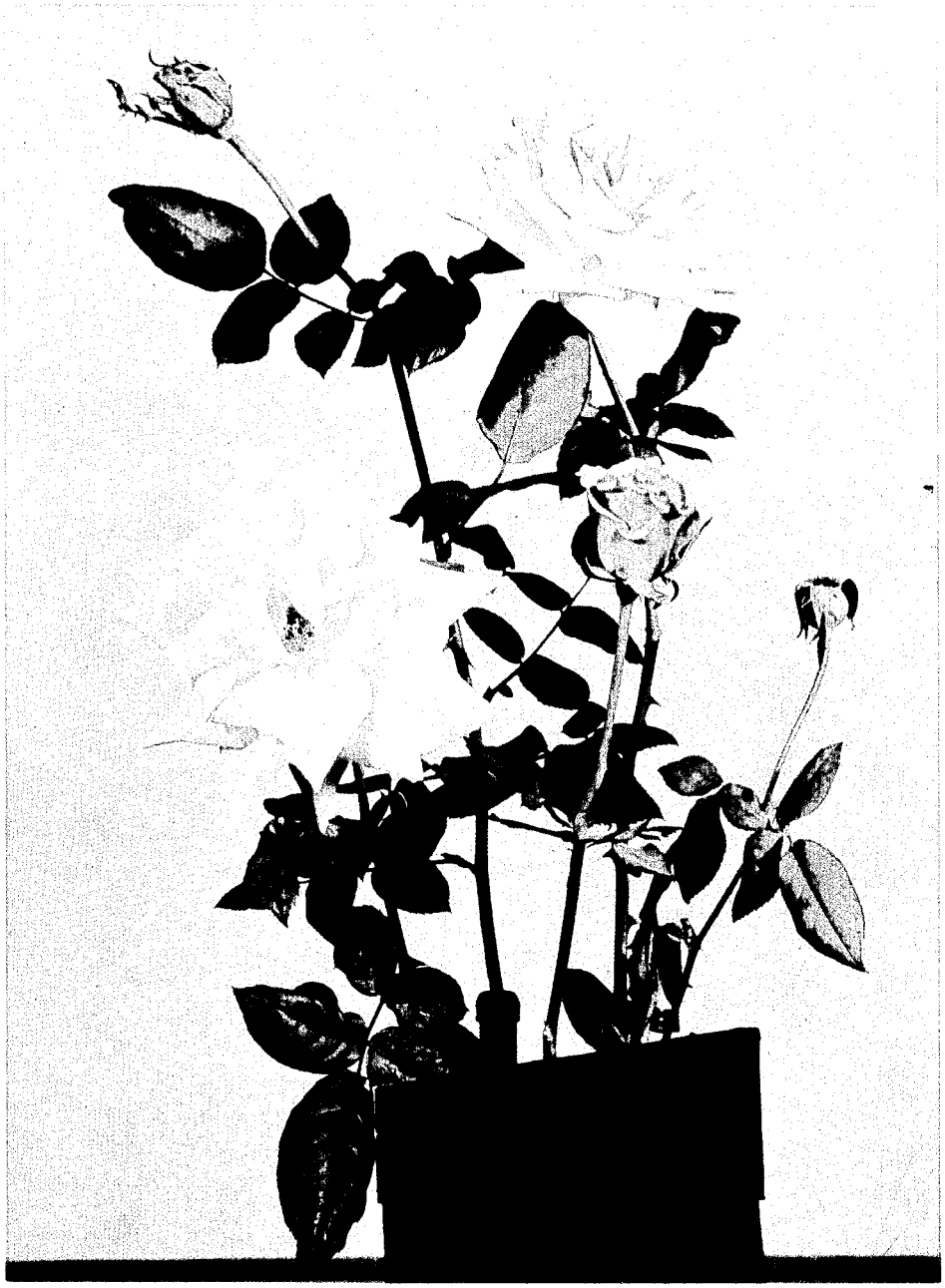
INVENTOR
H. C. Swim and O. L. Weeks
BY Robb & Robb
ATTORNEYS United States Patent Office Plant Pat. 1,985
Patented Nov. 15, 1960

1,985

ROSE PLANT

Herbert C. Swim, 1329 College Way, Ontario, Calif., and O. L. Weeks, Chino, Calif.

Filed Feb. 4, 1960, Ser. No. 6,832

1 Claim. (Cl. 47—61)

The present invention relates to a new and distinct variety of rose plant of the grandiflora class, which was originated by us by crossing the variety "Circus" (Plant Patent No. 1,382) with the variety "Golden Scepter" (Plant Patent No. 910).

As the result of this breeding, we have achieved a new rose variety which is endowed with the following unique combination of characteristics which are outstanding therein and which distinguish it from its parents, as well as from all other varieties of which we are aware:

(1) High productivity of good quality flowers which are suitable for cut flowers when grown under greenhouse conditions;

(2) A habit of bearing singly a high proportion of the flowers;

(3) A large flower size generally comparable to that of varieties of the hybrid tea class and substantially larger than that of most floribundas;

(4) Uniform flower petalage; and (5) A general color tonality of the flowers which is a distinctive multi-color gold and yellow blend.

In comparison with its seed parent, "Circus," the new variety is taller growing in its habit of growth, has longer stems on the individual flowers, produces more of its flowers singly than is usually the case of this parent, and the flowers are approximately half again larger than those of the variety "Circus."

As compared with its pollen parent, "Golden Scepter," the new variety has more thorns, greater flower petalage, approximately 6 more petals per flower, the flowers are a multi-color in contrast with the pure yellow flowers of this parent and there is substantially more anthocyanin pigment in the foliage and which is visible even on casual observation, as compared with the foliage of the pollen parent.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company Incorporated, of Baltimore, Maryland, except where general color terms of ordinary dictionary significance are obvious:

Type: Hardy; tall; bush; greenhouse and outdoors; seedling; for cut flowers and for garden decoration.

Class: Grandiflora.

Breeding: Seedling.

*Seed parent.*—"Circus."

*Pollen parent.*—"Golden Scepter."

Propagation: Holds its distinguishing characteristics through succeeding propagations by budding.

*Flower*

Locality where grown and observed: Chino, California.

Flowers borne: Singly and 2 or 3 or more to stem; in irregular clusters; on stems of medium length and normal strength.

Quantity of bloom: Abundant, both outdoors and in greenhouse.

Continuity: More or less continuous both during the outdoor growing season and under glass.

Fragrance: From slight to moderate. Nature—tea.

Bud:

*Peduncle.*—Long; medium heavy; erect; numerous stalked glands and small prickles. Color—near Strong Yellow Green, Plate 2.5GY 6/8.

*Before calyx breaks.*—Size—medium. Form—short; pointed; without a conspicuous neck; usually without foliaceous appendages on the surface of the bud; with bristle-like parts extending beyond the tip of the bud equal to ¼ of its length. Color—near Strong Orange, Plate 2.5YR 7/10.

*As calyx breaks.*—Color—near Strong Reddish Orange, Plate 7.5R 5/13, with some areas of Dark Reddish Orange, Plate 7.5R 4/11, except at base where color changes somewhat abruptly to Vivid Yellow, Plate 2.5Y 8/12.

*As first petal opens.*—Size—medium. Form—ovoid. Color: outside—near Strong Orange, Plate 2.5YR 7/10 over most of petal, but overlaid with Strong Red, Plate 2.5R 5/10 where touched by first light as flower opens, and at base where color is Vivid Yellow, Plate 2.5Y 8/12; inside—near Moderate Orange Yellow, Plate 10YR 8/10, except at base which is somewhat nearer Vivid Yellow, Plate 2.5Y 8/12. Opening—opens up well; is not retarded or prevented from opening by cold, hot, wet or dry weather.

Bloom:

*Size (when fully open).*—From medium to large; from 4 inches to 4½ inches.

*Petalage.*—Double; from 21 to 28 or occasionally more petals; arranged regularly.

*Form.*—High-centered; petals being at first very loosely rolled outward, but later becoming more tightly rolled outward at maturity.

Petals:

*Texture.*—Thick; leathery. Inside—satiny. Outside—satiny.

*Shape.*—Outside—nearly round. Intermediate—broadly obovate. Inside—obovate.

This description of a newly opened flower was made from a rose grown in a greenhouse in the month of November at Chino, California:

*Color.*—Outer petal: outside surface—between Strong Yellowish Pink, Plate 10R 7/9 and Strong Orange, Plate 2.5YR 7/10, except at base which is Vivid Yellow, Plate 2.5Y 8/12 and where the latter blends with the former in an area from ⅛ to ½ inch from point of attachment; on the portion exposed to light as the calyx breaks in the developing bud, there is an overlay of Deep Pink, Plate 2.5R 6/11 to Strong Red, Plate 2.5R 5/12, with the latter usually only at the extreme tip or apex; inside surface—near Moderate Orange Yellow, Plate 7.5YR 8/8 over most of petal, but with overlay of Strong Red, Plate 2.5R 8/12 sometimes on small area at apex and changing to Vivid Yellow, Plate 2.5Y 8/12 at base and blending with this latter color beginning about ⅝ inch from base. Intermediate petal: outside surface—near Moderate Orange Yellow, Plate 7.5YR 8/8, except at base where color is Vivid Yellow, Plate 2.5Y 8/12 and approaching the base where these two colors blend between ¼ and ½ inch from base; inside surface—between Moderate Orange Yellow, Plate 10YR 8/10 and Pale Orange Yellow, Plate 7.5YR 9/4, except at base which is Vivid Yellow, Plate 2.5Y 8/12 and area about ½ inch from base where these colors blend. Inner petal: outside surface—near Moderate Orange Yellow, Plate 7.5YR 8/8, except at base where color is Vivid Yellow, Plate 2.5Y 8/12 and area from ¼ to ½ inch from base where these colors blend; inside surface—between Moderate Orange Yellow, Plate 10YR 8/8 and Pale Orange Yellow, Plate 7.5YR 9/4, except at base which is Vivid Yellow, Plate 2.5Y 8/12 and area from ⅜ to ¾ inch from base where these colors blend.

This description was made from a rose that was open for three days in a greenhouse in the month of November at Chino, California:

*Color.*—Outer petal: outside surface—from near Deep Pink, Plate 10RP 6/12, through Moderate Pink, Plate 5R 8/6 over major portion, blending with and progressing to Brilliant Yellow, Plate 5Y 9/9 at base; inside surface—near Light Yellowish Pink, Plate 7.5R 9/3 over upper ⅓ of petal, blending with and eventually overcome with yellow tones progressing toward base which is Vivid Yellow, Plate 5Y 8/12. Inner petal: outside surface—from Pale Orange Yellow, Plate 7.5YR 9/4 to Brilliant Yellow, Plate 5Y 9/9 at base; inside surface—near Pale Orange Yellow, Plate 7.5YR 9/4 over upper ½ of petal, but changing to Brilliant Yellow, Plate 5Y 9/9 and then to Vivid Yellow, Plate 5Y 8/12 at base.

*General color effect.*—Newly opened flower—near Moderate Orange Yellow, Plate 10YR 8/10. 3-days open—near Brilliant Yellow, Plate 5Y 9/9.

*Behavior.*—Drop off cleanly; fading lighter; not especially affected by hot, wet or dry weather.

*Flower longevity.*—Cut roses grown in greenhouse and kept at living-room temperatures—5 days in November.

*Reproductive organs*

Stamens: Medium number; arranged irregularly about pistils.

Filaments: Medium length; most with anthers. Color—Brilliant Yellow, Plate 5Y 9/9.

Anthers: From small to medium size; open at various times. Color—near Moderate Orange Yellow, Plate 10YR 8/10.

Pollen: Moderate. Color—gold.

Pistils: Medium number.

Styles: Uneven; short; medium caliper; loosely bunched.

Stigma: Color—yellowish.

Ovaries: Most enclosed in calyx, but some protruding therefrom.

Hips: Globular; without conspicuous neck; smooth; walls thick and fleshy. Color—from green to yellow.

Sepals: Permanent; moderate length; recurved.

Seeds: Few; medium size.

*Plant*

Foliage:

*Leaves.*—Compound of 5 to 7 leaflets; normal quantity; medium size; moderately heavy; leathery.

*Leaflets.*—Shape—ovoid, with apex acute. Base—rounded. Margin—simply serrate.

*Color.*—Mature: upper surface—near Moderate Olive Green, Plate 7.5GY 4/4; under surface—between Brilliant Yellowish Green, Plate 7.5GY 8/7, and very Light Bluish Green, Plate 7.5BG 8/5. Young: upper surface—near Dark Red, Plate 2.5R 3/7; under surface—near Dark Red, Plate 5R 3/7.

*Rachis (the supporting stem of the compound leaf).*—Medium caliper. Upper side—grooved; sparsely glandular. Under side—moderately prickly; otherwise usually smooth.

*Stipules.*—Moderately short; from narrow to medium width; with very short points turning out at an angle of 45°.

*Disease resistance.*—Good resistance to mildew under both greenhouse conditions and in the garden, as compared with other varieties grown under comparable cultural conditions at Chino, California.

Growth:

*Habit.*—Bushy, upright-spreading; much-branched.

*Growth.*—Very vigorous.

*Canes.*—Medium caliper.

*Main stems.*—Color—between Dark Greenish Yellow, Plate 10Y 6/7 and Moderate Yellow Green, Plate 2.5GY 5/5. Large prickles—several; long; straight; with short elliptical base; color—grey-brown. Small prickles—color—grey-brown. Hairs—few; color—grey-brown.

*Branches.*—Color—between Light Yellow Green, Plate, 7.5GY 9/4, and Light Yellowish Green, Plate 10GY 8/7. Large prickles—several; long; straight; with short broad base; color—brown. Small prickles—few; color—brown. Hairs—few; color—brown.

*New shoots.*—Color—base color near Light Yellowish Green, Plate 2.5G 8/6, with faint overlay of Deep Purplish Red, Plate 10RP 3/10. Large prickles—several; long; straight; with short broad base; color—purple, with light green tip. Small prickles—few; color—purple, with light green tip. Hairs—none.

We claim:

A new and distinct variety of rose plant of the grandiflora class, substantially as herein shown and described, characterized particularly as to novelty by the unique combination of high productivity of flowers of good quality suitable for cut flowers when grown under greenhouse conditions, with a relatively high proportion of the flowers borne singly, a relatively large flower size comparable to that of varieties of the hybrid tea class and substantially larger than most varieties of the floribunda class, relatively uniform flower petalage, and a multicolor general color tonality of the flowers characterized by a distinctive gold or yellow color blend.

No references cited.